United States Patent [19]

Swerdloff et al.

[11] Patent Number: 4,624,695

[45] Date of Patent: Nov. 25, 1986

[54] O-DIAMINOPHOSPHINYL DERIVATIVES OF OXIMES AS UREASE INHIBITORS

[75] Inventors: Michael D. Swerdloff, Parsippany; Milorad M. Rogic, Whippany, both of N.J.; Larry L. Hendrickson, Camillus, N.Y.

[73] Assignee: Allied Corporation, Morris Township, Morris County, N.J. ; '

[21] Appl. No.: 563,348

[22] Filed: Dec. 20, 1983

[51] Int. Cl.$^4$ .................... A01N 57/26; A61K 31/66; C07F 9/02

[52] U.S. Cl. .......................................... 71/86; 71/87; 514/89; 514/90; 514/91; 514/92; 514/95; 514/107; 514/108; 514/112; 514/113; 514/118; 544/63; 544/157; 546/22; 548/112; 548/413; 549/6; 558/386; 560/35; 560/168; 564/14

[58] Field of Search ................. 564/14; 424/220, 211; 260/465 E; 71/86, 87; 514/89, 90, 91, 92, 95, 107, 108, 112, 113, 118; 544/63, 157; 546/22; 548/112, 413; 549/6; 558/386; 560/35, 168

[56] References Cited

U.S. PATENT DOCUMENTS 4,182,881  1/1980  Bayless et al. ..................... 546/22
4,222,948  9/1980  Alaimo et al. ............... 260/397.7 R
4,225,526  9/1980  Alaimo et al. ............... 260/397.7 R
4,242,325  12/1980 Bayless et al. ....................... 424/210

FOREIGN PATENT DOCUMENTS 122177   9/1976   German Democratic Rep. .
122621   10/1976  German Democratic Rep. .
130936   5/1978   German Democratic Rep. .
142714   7/1980   German Democratic Rep. .
1494774  12/1977  United Kingdom .

OTHER PUBLICATIONS

M. Nakanishi and T. Oe, Japan Pat. No. 7379, Chem. Abstr. 1967, vol. 67, 81947x.

*Primary Examiner*—Dolph H. Torrence
*Attorney, Agent, or Firm*—Richard C. Stewart; Gerhard H. Fuchs

[57] ABSTRACT

The invention relates to novel urease inhibited fertilizer compositions containing urea and a urease inhibiting amount of one or more o-diaminophosphinyl derivatives of oximes, and methods and composition for inhibiting the activity of urease through use of such compounds.

31 Claims, No Drawings

O-DIAMINOPHOSPHINYL DERIVATIVES OF OXIMES AS UREASE INHIBITORS

BACKGROUND OF THE INVENTION

1. Field of the Invention

This invention relates to urease inhibited urea based fertilizer compositions. More particularly, this invention relates to urease inhibited urea based fertilizer compositions which contain certain oximated diaminophosphinyl compounds as the urease inhibitors, and to methods and compositions for inhibiting the action of soil urease through use of such compounds.

2. The Prior Art

It is well know in the art to use urea and urea compositions in fertilizers, for application to the soil. The effective life of such fertilizers, however, is of short duration wherever microbiological activity exists in the soil to which the fertilizer is applied. This is due to the fact that urea is hydrolyzed rapidly, and nitrogen is lost in the form of ammonia, when urea is placed under or on the surface of soil which contains urease. Urease, a crystallizable enzyme occurring in numerous bacteria and fungi, as for example *Micrococcus urease,* catalyzes the conversion of urea into ammonia and carbon dioxide. The reactions are as follows:

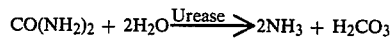

A portion of the ammonia thus formed is held by absorbing constituents of the soil and is available to plants as nutrient. However, a large amount of the ammonia may be lost to the air. A further problem resulting from the action of urease is the accumulation of ammonium in the soil which can damage germinating seedlings and young plants.

One approach to the reduction of problems resulting from the activity of soil urease toward soil applied urea is to find compounds that inhibit urease activity when applied to soils in conjunction with fertilizer urea. This approach has received considerable attention, and several classes of compounds have been used as urease inhibitors.

For example, certain prior art describes various phosphoro compounds which are useful as urease inhibitors. Illustrative of such prior art are East German Pat. Nos. 142,714; 212,026; 122,177; 122,621 and 130,936, and Great Britain Pat. No. 1,494,774 which describe various phosphorodiamidate compounds as urease inhibitors. Also exemplary of such prior art is U.S. Pat. No. 4,242,325 which describes a method of controlling the enzymatic decomposition of urea to ammonia and carbonic acid due to the action of urease which comprises exposing the enzyme to certain phosphoric triamide compounds. U.S. Pat. No. 4,182,881 describes the use of certain N-[diaminophosphinyl]arylcarboxyamide compounds as inhibitors of the enzyme urease in the urinary tract. U.S. Pat. No. 4,225,526 describes the use of 8-[(4-aminophenyl)sulfonyl]amino-2-naphthalenyl phosphorodiamidate compounds as inhibitors of the enzyme urease, and U.S. Pat. No. 4,222,948 describes the use of ([(4-aminophenyl)sulfonyl]amino)phenyl phosphorodiamidates as inhibitors of the enzyme urease. Nakanishi, M, and Oe, T., Japan Patent 7379; Chem. Asbtr. 1967, 67, 81947X describes certain diaminophosphinyl compounds containing oxidized sulfur functions and discloses that such compounds are useful in treating diabetes mellitus.

SUMMARY OF THE INVENTION

In accordance with the present invention, there is provided a unique fertilizer composition comprising urea or one or more compounds which are capable of forming urea in situ when subjected to the use conditions of the composition, and a "urease inhibiting effective amount" of one or more compounds of the formula:

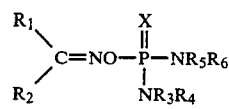

wherein:

X is oxygen or sulfur;

$R_1$ and $R_2$ are the same or different and are hydrogen, substituted or unsubstituted alkyl or aryl groups, or $R_1$ and $R_2$ together may form a substituted or unsubstituted divalent aliphatic chain completing a cycloaliphatic group, which may optionally include one or more divalent heteroatoms of oxygen, sulfur or nitrogen, wherein permissible substituents include one or more alkyl, aryl, halogen, trihalomethyl, nitro, cyano, alkanoyl, alkyl, carboxylate, arylcarboxylate, alkoxy, hydroxy, alkylmercapto, arylmercapto, mercapto, amino, alkylamino, dialkylamino, arylamino, diarylamino, diaminophosphinyl, N-diaminophosphinyl, O-diaminophosphinyl, S-diaminophosphinyl, carbamoyl and carbamoyldiaminophosphinyl; and $R_3$, $R_4$, $R_5$ and $R_6$ are the same or different and are hydrogen or alkyl having from about 1 to about 4 carbon atoms.

Hereinafter, the aforementioned compounds are referred to as "oximated O-diaminophosphinyl derivatives".

Another aspect of this invention relates to a method of enhancing the yield of plants which comprises applying the composition of this invention to a plant growth medium within reach of the plant's root system, (hereinafter referred to as "root zone"). The term "plant growth medium" as herein employed refers to various natural and artificial medium which support plant growth, including soil, potting mixtures of organic and inorganic matter, and artificial medium such as polyurethane foams.

Yet another aspect of this invention relates to a composition comprising a "urease inhibiting effective amount" of one or more oximated O-diaminophosphinyl derivatives, which composition is useful for carrying out the aforementioned, method. As used herein "urease inhibiting effective amount" is an amount of one or more of the said oximated O-diaminophosphinyl derivatives compounds which when admixed with urea (or one or more urea precursor compounds capable of forming urea in situ under the use conditions of the composition); or when applied to a situs, as for example a plant growth medium is capable of inhibiting the catalytic activity of urease that may be in or at the medium or other situs to any extent.

It has been discovered by applying a urease inhibiting effective amount of one or more of the oximated O-diaminophosphinyl derivatives to a plant growth medium or other situs the urease catalyzed hydrolysis of urea which may be present at the situs to ammonia is suppressed, thereby preventing the rapid loss of urea from the situs or medium. Furthermore, by proper distribution and/or application of the one or more oximated O-diaminophosphinyl derivatives; this action of inhibiting the urease catalyzed hydrolysis of urea to ammonia is effective over a prolonged period of time.

DETAILED DESCRIPTION OF THE INVENTION

The application and/or distribution of a urease inhibiting effective amount of one or more of the above-identified oximated O-diaminophosphinyl derivatives to a situs, such as a plant growth medium, or inclusion thereof in a composition and application and/or distribution of the composition to a situs is essential for the practice of this invention. While, the oximated O-diaminophosphinyl derivatives can be used to inhibit the urease catalyzed hydrolysis of urea at any situs, they are especially useful for such inhibition in an agricultural context by application to a plant growth medium. In these preferred embodiments, usually, an acceptable level of urease inhibition can be achieved if at least about 0.01 parts by weight of said one or more oximated O-diaminophosphinyl derivatives per one million parts by weight of soil or other plant growth medium. Hereinafter the abbreviation "p.p.m." is used to refer to parts by weight of one or more oximated O-diaminophosphinyl derivatives per one million parts by weight of plant growth medium. In the preferred embodiments of this invention, the amount of said one or more oximated O-diaminophosphinyl derivatives distributed in the said medium is from about 0.01 p.p.m. to about 5,000 p.p.m., and in the particularly preferred embodiments of the invention is from about 0.2 p.p.m. to about 1,000 p.p.m. Amongst these particularly preferred embodiments of the invention, most preferred are those embodiments of the invention in which the amount of said one or more oximated O-diaminophosphinyl derivatives distributed in said medium is from about 1 p.p.m. to about 500 p.p.m.

Within the aforementioned limitations, the preferred amounts of the one or more oximated O-diaminophosphinyl derivatives impregnated or distributed in the plant growth medium are dependent upon the particular situation. Thus, in determining the amount to be employed, consideration is made not only of the treatment need, i.e., soil pH, temperature, soil type, and the like, but also of the mode of application to the plant growth medium. When the one or more oxidated O-diaminophosphinyl derivatives are to be applied in a broadcast application, the amount in p.p.m. may frequently be less than in row or band application where, for a substantial depth and width within the vicinity of application, there can be a very high concentration of the one or more such compounds. When application is made near the root zone of growing plants, or when application is made immediately prior to seeding or transplanting, the amounts supplied are frequently at a lower rate than when application is made at the end of the growing season to prepare the plant growth medium for the following season. By dispersing very large dosages in the plant growth medium, a prolonged inhibition of urease activity can be obtained over a period of many months. The concentration of the one or more oximated O-diaminophosphinyl derivatives is eventually reduced to a minimum by decomposition in the plant growth medium.

In one method for carrying out the present invention, one or more oximated O-diaminophosphinyl derivatives are distributed throughout the plant growth medium in a broadcast application, such as by spraying, dusting, distributing in irrigation water and the like. In such application, the one or more oximated O-diaminophosphinyl derivatives are supplied in amounts sufficient to permeate the growing area of the medium with a urease inhibiting effective amount of such oximated O-diaminophosphinyl derivatives. In field administration, the one or more oximated O-diaminophosphinyl derivatives can be distributed in the plant growth medium in an amount and through such cross-section of the medium as to provide for the presence therein of a urease inhibiting effective amount of the one or more oximated O-diaminophosphinyl derivatives. It is usually preferred that the one or more oximated O-diaminophosphinyl derivatives be distributed in the plant growth medium to a depth of at least two inches below the surface of the plant growth medium.

In another method for carrying out the present invention, one or more oximated O-diaminophosphinyl derivatives are administered to the plant growth medium in a band or row application. In such application, administration is made with or without carrier in amounts sufficient to supply to the soil or other plant growth medium a urease inhibiting effective amount of the one or more oximated O-diaminophosphinyl derivatives. After administration with or without discing or dragging, subsequent irrigation or rainfall distributes the one or more oximated O-diaminophosphinyl derivatives throughout the plant growth medium.

In one embodiment of the present invention, the one or more oximated O-diaminophosphinyl derivatives are distributed throughout the growth medium prior to seeding or transplanting the desired crop plant.

In another embodiment, the soil or plant growth medium within the root zone of growing plants is treated with the one or more oximated O-diaminophosphinyl derivatives in an amount effective to inhibit the action of urease, but sublethal to plant growth. By following such practice, no adverse effect is exerted by the one or more oximated O-diaminophosphinyl derivatives upon growth of seeds or plants. Oftentimes, it is desirable to treat the soil adjacent to plants, and this procedure may be carried out conveniently in side-dressing operations.

In a further embodiment of the invention, soil or other plant growth medium is treated with one or more oximated O-diaminophosphinyl derivatives following harvest to prevent rapid loss of urea, and to prevent build-up of soil urease. Such practice conserves the soil nitrogen for the following growing season. In such application, the upper limit is primarily an economic consideration.

In an additional embodiment, the soil or plant growth medium can be impregnated with the one or more oximated O-diaminophosphinyl derivatives in conjunction with the application of urea or one or more urea precursor compounds capable of forming urea in situ on application to the plant growth medium. Urea is a well known, commercially available compound and will not be discussed herein in detail. Illustrative of compounds which are believed to form urea on addition to the soil and are water soluble and formaldehyde condensation products, as for example methylolureas, methyleneureas and mixtures thereof. These products and a method for their preparation is described in detail in Justice U.S. Pat. No. 3,462,256. Still other useful sources of urea are water-insoluble urea formaldehyde condensation products such as ureaform. Illustrative of useful water-insoluble urea and formaldehyde condensation products are those whose preparation and use are described in detail in U.S. Pat. Nos. 3,677,736 and 4,033,745.

The present invention can be carried out by distributing one or more oximated O-diaminophosphinyl derivatives in an unmodified form through a plant growth medium. The present method also embraces distributing one or more such compounds as a constituent in liquid or finely divided solid compositions.

The concentration of one or more oximated O-diaminophosphinyl derivatives in compositions to be employed for the treatment of plant growth medium is not critical and can vary considerably provided the required dosage of the effective agents is supplied to the growth medium. In general, good results are obtained with liquid and/or solid compositions containing at least about 0.00001 percent by weight of the one or more oximated O-diaminophosphinyl derivatives. Usually, however, the weight percent of the one or more oximated O-diaminophosphinyl derivatives is from about 0.0001 percent to about 98 percent by weight on the same basis. In the preferred embodiments of the invention, the amount of the one or more oximated O-diaminophosphinyl derivatives in the composition is from about 0.002 to about 50 weight percent, and in the particularly preferred embodiments is from about 0.01 to about 20 weight percent on the aforementioned basis. Liquid or dust compositions in which the one or more oximated O-diaminophosphinyl derivatives is present in higher concentration can be utilized as such or can be employed as concentrate compositions to be diluted to prepare actual treating compositions.

In such practice, the one or more oximated O-diaminophosphinyl derivative compounds can be modified with one or more additiments or soil treating adjuvants including water, petroleum distallates or other liquid carriers, surface-active dispersing agents, inert finely divided solids, and fertilizers, as for example urea, the aforementioned urea precursor compounds, and reduced nitrogen fertilizers such as ammonium nitrate and ammonia. These adjuvants cooperate with the one or more oximated O-diaminophosphinyl derivatives so as to facilitate the practice of the present invention and to obtain an improved result. Preferred adjuvants are surface-active dispersing agents, inert finely divided solids and urea and/or urea precursor compounds. The amount of urea or urea precursor compound which may be included in the composition of this invention is not critical to the unique advantages thereof, and any amount known to those of skill in the art for use in fertilizers can be used. Normally, the amount employed will vary widely depending on a number of factors, including the times and frequency of application. In the preferred embodiments of the invention, the quantity of urea or urea precursor compound may vary from about 0.5 to about 95 weight percent based on the total weight of the composition and in the particularly preferred embodiments may vary from about 1 to about 50 weight percent on the same basis. In the most preferred embodiments of this invention, the quantity of urea or urea precursor compound will vary from about 3 to about 40 weight percent on the aforementioned basis.

The composition of this invention may include other optional ingredients known to those of skill in the art for inclusion in fertilizer compositions. For example, the composition may include sources of potassium, sulfur, phosphorus, boron, zinc, iron, manganese, copper, molybdenum, cobalt and like micronutrient and macronutrients which may be deficient in the soil. The composition may also include plant growth regulators, as for example auxins, cytokinins and the like, as well as pesticides, such as insecticides, miticides, herbicides, nematocides and the like. Moreover, the fertilizer composition can include sources of nitrogen other than urea, as for example ammonium nitrate and the like, and other materials which increase nitrogen efficiency, as for example, other urease inhibitors and nitrification inhibitors. Depending upon the concentration of the one or more oximated O-diaminophosphinyl derivatives, augmented compositions can be distributed in the plant growth medium without further modification or can be considered as concentrates and subsequently diluted with additional inert carrier to produce the ultimate treating composition.

Liquid compositions containing the desired amount of the one or more oximated O-diaminophosphinyl derivatives can be prepared by dispersing the latter in one or more liquid carriers such as water or an organic solvent with or without the aid of a suitable surface active dispersing agent or emulsifying agent. Suitable organic solvents include acetone, diisobutylketone, methanol, ethanol, isopropyl alcohol, diethyl ether, toluene, methylene chloride, chlorobenzene and petroleum distillates. The preferred organic solvents are those which are of such volatility that they leave little permanent residue in the growth medium. Dispersing and emulsifying agents which can be employed in liquid compositions include condensation products of alkylene oxides with phenols and organic acids, alkyl aryl sulfonates, polyoxyalkylene derivatives or sorbitol ester, sugar esters, complex ether alcohols, mahogany soaps and the like. The surface active agents are generally employed in the amount of from about 1 to about 20 percent by weight of the oximated O-diaminophosphinyl derivatives and preferably in an amount of from about 1 to about 10 weight percent on the same basis.

Solid compositions containing the active one or more oximated O-diaminophosphinyl derivatives can be prepared by dispersing the latter in finely divided inert solid carriers such as talc, chalk, gypsum, vermiculite, bentonite and the like, fuller's earth, attapulgite and other clays, various solid detergent dispersing agents and solid fertilizer compositions. In preparing such compositions, the carrier is mechanically ground with a solid one or more oximated O-diaminophosphinyl derivatives; or wet with a liquid one or more oximated O-diaminophosphinyl derivatives; or wet with a solution or dispersion of a solid or liquid one or more oximated O-diaminophosphinyl derivatives in a volatile organic solvent. Depending upon the proportions of ingredients, these compositions can be employed without further modification or be considered concentrates and subsequently further diluted with solid surface active dispersing agents, talc, chalk, gypsum, bentonite, diatomaceous earth, fullers earth, or the like to obtain the desired treating composition. Furthermore, such concentrate compositions can be dispersed in water with or without added dispersing agent or agents to prepare aqueous soil treating compositions.

The required amount of the one or more oximated O-diaminophosphinyl derivatives contemplated herein may be applied per acre treated in from about 1 to about 200 gallons or more of liquid carrier and/or diluent or in from about 5 to about 500 pounds of inert solid carrier and/or diluent. The concentration in the liquid concentrate will usually vary from about 10 to about 95 percent by weight and in the solid formulations from about 0.5 to about 90 percent by weight. Satisfactory sprays, dusts, or granules for general use contain from about ¼ to about 15 pounds of active one or more oximated O-diaminophosphinyl derivatives per acre.

The compounds contemplated herein prevent or retard the urease catalyzed hydrolysis of urea, and they have relatively high residual activity. With respect to plants they have a high margin of safety in that when used in sufficient amount to inhibit the activity of urease, they do not burn or injure the plant, and they resist weathering which includes wash-off caused by rain, decomposition by ultra-violet light, oxidation, or hydrolysis in the presence of moisture or, at least such decomposition, oxidation, and hydrolysis as would materially decrease the desirable urease inhibiting characteristic of the compounds or impart undesirable characteristics, for instance, phytotoxicity, to the compounds. The compounds are so chemically inert that they are compatible with substantially any other constituents of the spray schedule, and they may be used in the soil, upon the seeds, or the roots of plants without injuring either the seeds or roots of plants.

While the composition and method of this invention are particularly suited for agricultural applications for prevention or inhibition of urease catalyzed hydrolysis of urea, they can also be used in other applications where inhibition of the activity of urease is desired. For example, such other applications include use in animal litters, as feed additives, pharmaceutical applications, diaper treatment, urease inhibition in mammalian urinary tracts, and the like. It should be noted that while all of the above-identified compounds exhibit urease inhibiting activity, the particular active compound employed in one application may not necessarily be useful in another application. Thus, in the selection of a particular active compound for use in an application, such factors are toxicity of the compound, the environment in which the compound will be used, level of urease inhibition desired and the like must be considered in selecting a particular compound for use.

Oximated O-diaminophosphinyl derivatives which are useful as urease inhibitors in the composition of this invention are those of the formula:

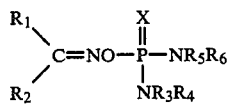

wherein:
X is oxygen or sulfur;
$R_1$ and $R_2$ are the same of different and are hydrogen, substituted or unsubstituted alkyl or aryl groups or $R_1$ and $R_2$ together may form a substituted or unsubstituted divalent aliphatic chain completing a cycloaliphatic group, which may optionally include one or more divalent heteroatoms of oxygen, sulfur or nitrogen wherein permissible substituents include one or more alkyl, aryl, halogen, trihalomethyl, nitro, cyano, alkanoyl, alkyl, carboxylate, arylcarboxylate, alkoxy, hydroxy, alkylmercapto, arylmercapto, mercapto, amino, alkylamino, dialkylamino, arylamino, diarylamino, diaminophosphinyl, N-diaminophosphinyl, O-diaminophosphinyl, S-diaminophosphinyl, carbamoyl and carbamoyldiaminophosphinyl; and $R_3$, $R_4$, $R_5$ and $R_6$ are the same or different and are hydrogen or alkyl having from about 1 to about 4 carbon atoms.

Examples of $R_1$ and $R_2$ include methyl, hydrogen, ethyl, isopropyl, tert-butyl, n-octyl, cyclohexyl, trichloromethyl, trifluoromethyl, 2-chloroethyl, phenyl, p-tolyl, 4-nitrophenyl, 3-trichloromethylphenyl, 3-chlorophenyl, 2-nitrophenyl, N,N-diphenylamino, 4-morpholino, pentamethyleneamino, N,N-dicyclohexylamino, N-diaminophosphinyl, 4-[O-(diaminophosphinyl)phenyl], 4-[N-(diaminophosphinyl)phenyl], 3-cyanophenyl, and the like, or $R_1$ and $R_2$ together may form cycloaliphatic moieties such as cyclopentyl, cyclohexyl, cyclooctyl, thienyl, norbornyl, camphor, adamantyl, cyclododecyl, 4-tert-morpholinyl, butylcyclohexyl, thiazolidinyl, piperdyl, pyrrolydyl, oxazinyl, oxazinonyl, and the like.

Examples of $R_2$ include hydrogen, methyl, ethyl, phenyl, 2-chloroethyl, 4-nitrophenyl, 3-methyoxyphenyl, 2-methylmercaptoethyl, and the like.

Examples of $R_3$, $R_4$, $R_5$, and $R_6$ include hydrogen, methyl, ethyl, n-propyl, isopropyl, and tert-butyl.

Illustrative of other such compounds within the scope of the above-referenced generic formula which can be used in the practice of the invention are:
O-(Diaminophosphinyl)acetaldehyde oxime
O-(Diaminophosphinyl)-2-butanone oxime
O-(Diaminophosphinyl)formaldehyde oxime
O-(Diaminophosphinyl)benzaldehyde oxime
O-(Diaminophosphinyl)acetophenone oxime
O-(Diaminophosphinyl)cyclohexanone oxime
O-(Diaminophosphinyl)-3-hexanone oxime
O-(Diaminophosphinyl)benzophenone oxime
O-(Diaminophosphinyl)cyclopentanone oxime
O-(Diaminophosphinyl)-4-tert-butylcyclohexanone oxime
O-(Diaminophosphinyl)camphor oxime
O-(Diaminophosphinyl)-4-nitrobenzaldehyde oxime
O-(Diaminophosphinyl)-2-chloroacetophenone oxime
O-(Diaminophosphinyl)-4-methoxybenzophenone oxime
O-(Diaminophosphinyl)-2-chlorocyclohexanone oxime
O-(Diaminophosphinyl)-2,6-dimethyl-4-heptanone oxime
O-(Diaminophosphinyl)-3-phenoxy-2-propanone oxime
O-(Diaminophosphinyl)-5-chloro-2-pentanone oxime
O-(Diaminophosphinyl)-4-phenyl-2-butanone oxime
O-(Diaminophosphinyl)-1-methyl-4-piperidone oxime
O-(Diaminophosphinyl)acetylpyridine oxime
O-(Diaminophosphinyl)-4-methyl-1-tetralone oxime
O-(Diaminophosphinyl)-6-methyl-2-pyridine carboxaldehyde oxime
O-(Diaminophosphinyl)butyraldehyde oxime
O-(Diaminophosphinyl)-2-norbornone oxime
O-(Diaminophosphinyl)-6-methoxy-1-tetralone oxime
O-(Diaminophosphinyl)-3-fluorobenzaldehyde oxime
O-(Diaminophosphinyl)-4-bromoacetophenone oxime
O-(Diaminothiophosphinyl)acetaldehyde oxime
O-(Diaminothiophosphinyl)-2-propanone oxime
O-(Diaminothiophosphinyl)-2-butanone oxime
O-(Diaminothiophosphinyl)acetophenone oxime
O-(Diaminothiophosphinyl)benzaldehyde oxime O-(Diaminothiophosphinyl)benzophenone oxime
O-[N-Methyl-(diaminophosphinyl)]-2-propanone oxime
O-[N,N-Dimethyl-(diaminophosphinyl)]acetophenone oxime
O-[N,N'-Diethyl-(diaminophosphinyl)]benzaldehyde oxime
O-[N-Isopropyl-N'-methyl-(diaminophosphinyl)-]acetaldehyde oxime
O-[N-Butyl-N-ethyl-(diaminothiophosphinyl)]cyclohexanone oxime Preferred for use in the practice of this invention are compounds of the aforementioned generic formula in which:

X is oxygen and sulfur;

$R_1$ and $R_2$ are hydrogen, alkyl, aryl, or together form a cycloaliphatic group; and $R_3$, $R_4$, $R_5$ and $R_6$ are hydrogen.

Particularly preferred for use in the practice of this invention are compounds of the aforementioned generic formula in which:

X is oxygen or sulfur;

$R_1$ and $R_2$ are hydrogen or substituted or unsubstituted alkyl or aryl; and $R_3$, $R_4$, $R_5$ and $R_6$ are hydrogen.

Amongst these particularly preferred compounds most preferred are those compounds in which:

X is oxygen or sulfur;

$R_1$ and $R_2$ are hydrogen, substituted or unsubstituted alkyl or aryl provided that at least one of $R_1$ and $R_2$ is a primary alkyl or hydrogen; and $R_3$, $R_4$, $R_5$ and $R_6$ are hydrogen.

An especially effacious compound for use in practice of this invention is N-(diaminophosphinyl)-2-propanone oxime.

Compounds for use in the practice of this invention can be conveniently prepared in accordance with the following Reaction Scheme A:

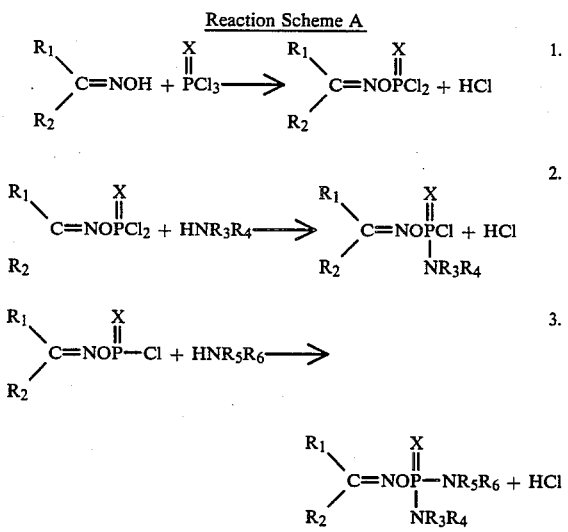

wherein $R_1$, $R_2$, $R_3$, $R_4$, $R_5$, $R_6$ and X are as identified hereinabove.

Alternatively, compounds for use in the practice of this invention can be prepared in according to the following Reaction Scheme B:

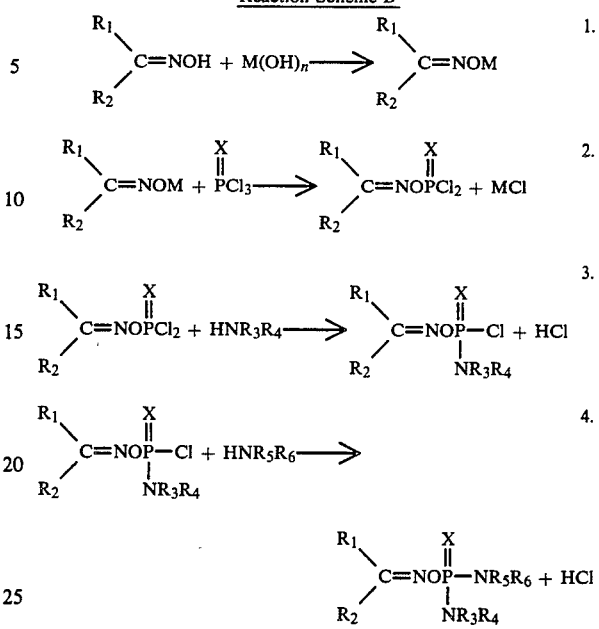

wherein $R_1$, $R_2$, $R_3$, $R_4$, $R_5$, $R_6$ and X are as described above and M is an inorganic metal such as sodium, potassium, calcium, magnesium and the like.

Briefly stated, in each step of the above reaction schemes substantially equal molar amounts or excesses of the reactants are contacted neat or in an inert solvent. Useful inert reaction solvents include ethyl ether, carbon tetrachloride, methylene chloride, benzene, dioxane, glyme, toluene, xylene, tetrahydrofuran, methyl sulfoxide, dimethylformamide and the like.

In those reaction steps of the above schemes in which hydrogen chloride is produced, such as reaction steps 1, 2 and 3 of Reaction Scheme A and reaction steps 3 and 4 of Reaction Scheme B a hydrogen chloride acceptor may be used. The hydrogen chloride acid acceptor employed is a basic material which can be either an inorganic or organic base. Suitable inorganic bases include alkali metal carbonates such as sodium carbonate, potassium carbonate and the like. Organic bases which are useful and preferred for use in this invention are tertiary amines, as for example pyridine, lutidine, 1,4-diazabicyclo[2.2.2]octane, isoquinoline, quinoline, N-methylpiperidine, trimethylamine, triethylamine, and the like.

Reaction temperatures are critical for reaction steps 1 and 2 of Reaction Scheme A, and reaction steps 2 and 3 of Reaction Schemes B because of the heat sensitivity of the oximated phosphorus oxychloride intermediate. These reaction steps are preferably carried out at a temperature of from about $-40°$ to about $+10°$ C., although higher temperatures up to about $+20°$ C. and lower temperatures down to about $-80°$ C. can be used. The reaction temperatures of the other reaction steps are not critical, these reaction steps can be conveniently carried out at a temperature of from about $-80°$ C. to about 200° C., but are preferably carried out at a temperature of from about $-40°$ C. to about 125° C.

Reaction pressures are not critical and can be varied widely. The reactions can be carried out at subatmospheric, atmospheric or super-atmospheric pressure.

However, for convenience the reactions are usually carried out at atmospheric or autogeneous pressure.

The order in which the reactants are reacted indicated in the reaction scheme is for illustrative purposes only, and the order of reactants is not critical. The exact proportions of the reactants are also not critical, some of the desired product being obtained when the reactants are employed in any proportions. However, in going to completion, the reaction consumes the reactants and the hydrogen chloride acceptor in substantially equimolar proportions and the use of the reactants and the hydrogen chloride acceptor in such proportions is preferred, although an excess of the acceptor can be used.

Reaction times are not critical and can be varied widely depending on such factors as the reaction temperature, reactivity of the reactants, and the like. The reaction mixture is usually held within the desired reaction temperature range for a period of time, conveniently from about 1 to about 24 hours before cooling. Good yields are obtained with reaction times of from 2 to about 5 hours.

After the reactions have gone substantially to completion, the product can be separated by such conventional procedures as evaporation, and purified by conventional procedures such as distillation and extraction. The product separated as described above can be employed in the control of urease in the soil or in other applications in accordance with this invention or may be further purified by conventional procedures such as extraction and distillation.

The following specific example is presented to more particularly illustrate the invention.

EXAMPLE I

The Preparation of O-(Diaminophosphinyl)-2-propanone Oxime

A. Into a dry, 3-neck, round bottom flask fitted with a mechanical stirrer, a condenser, and an addition funnel under a nitrogen atmosphere was placed 75 mL of ether, 20.2 mL (19.8 g, 0.25 mol) of pyridine, and 18.4 mL (30.7 g, 0.20 mol) of phosphorus oxychloride. The flask was cooled in an ice-bath to 0° C., and a solution of 14.6 g (0.20 mol) of acetone oxime in 75 mL of ether was added via the addition funnel over a 1 h period. Stirring was continued for another 1 h and the precipitated pyridine hydrochloride (25.1 g) was removed by filtration. The ether solution containing the intermediate dichloride was kept cold and used immediately in the next step. An attempt to isolate this material by evaporation of a small amount of this solution led to a violent decomposition.

B. Into a 3-neck, 1000 mL, round bottom Morton flask equipped with a dry-ice condenser, an air-driven mechanical stirrer, and an addition funnel was placed 300 mL of ether and about 50 mL of liquid ammonia. After allowing this mixture to equilibrate at about −30° C., the cold filtrate from step A above was added via the addition funnel over a 90 min period to the vigorously stirred solution. Copious amounts of a white solid formed during this procedure. The mixture was stirred for an additional 30 min while maintaining the temperature at about −30° C. The white solid was collected by filtration, washed well with 500 mL of ether, and dried under nitrogen to give 35.2 g (88%) of solid containing ammonium chloride and product. Twenty grams of this material was boiled with 300 mL of chloroform for 30 min. The hot mixture was filtered, and the filtrate was evaporated to give 8.74 g of white solid, mp 124°–130° C. This material was recrystallized from 225 mL of chloroform to give 5.83 g of white crystals, mp 125°–131° C.:

$^{31}$P NMR (DMSO-d$_6$): δ19.3 ppm (s).

$^1$H NMR (DMSO-d$_6$): δ4.0 (br s, 4H, NH$_2$) and 1.87 and 1.85 ppm (s, 3H each, CH$_3$).

$^{13}$C NMR (DMSO-d$_6$): δ160.62 (d, J$_{C-P}$=2.9 Hz, 1C, C=NO—), 21.16 (s, 1C, CH$_3$), and 15.92 ppm (s, 1C, CH$_3$).

Mass Spectrum (70 eV) of sample derivatized with "Methyl-8" reagent (DMF-Dimethylacetal) corresponding to (CH$_3$)$_2$C=NOP(O)[N=CHN)CH$_3$)$_2$]$_2$: m/e 261 (M+), 205 (M+—NC(CH$_3$)$_2$), 189 (M+—ONC(CH$_3$)$_2$), 162 (M+—ONC(CH$_3$)$_2$—HCN), 135, and 44.

Infrared (KBr): 3360 (s, NH$_2$), 3200 (s, NH$_2$), 3100 (s, NH$_2$), 1645 (w), 1570 (s), 1432 (m), 1382 (s), 1235 (s), 1050 (sh), 1020 (s), 900 (s), 838 (m), 810 (s), 600 (w), 550 (m), 500 (w), and 460 cm$^{-1}$(m).

Analysis: Calcd. for C$_3$H$_{10}$N$_3$O$_2$P: C, 23.84; H, 6.67; N, 27.81; P, 20.50. Found: C, 23.60; H, 6.68; N, 27.67; P, 20.10.

EXAMPLE II

Efficacy Test

Efficacy tests were conducted to evaluate the efficacy of certain representative oximated O-diaminophosphinyl compounds as urease inhibitors. The inhibition tests were run in a New York soil (Cazenovia silt loam, pH 7.2) or in Wisconsin soil (Plano silt loam, pH 5.4). Evaluations (run in triplicate) consisted of applying 800 micrograms of the test compound in 5 mL of water and 42.8 mg of urea in 1 mL of water to 20 g of air-dry soil in a glass bottle. The bottle was capped with perforated aluminum foil and incubated at 25° C. for three days prior to extraction with 100 mL of a 2M potassium chloride solution containing 0.5 mg of phenylmercuric acetate. The extracts were then analyzed for remaining urea using an autoanalyzer. Percent inhibition was calculated as $$\% \text{ Inhibition} = \left(1 - \frac{A - B}{A - C}\right) \times 100\%$$

where A is urea recovered from unincubated sample (urea added to soil and immediately extracted); B is urea recovered from inhibited sample; and C is urea recovered from the control (uninhibited sample).

The results of these tests are set forth in the following Table I.

TABLE I

| Compound | % Inhibition | |
|---|---|---|
| | Cazenovia (pH 7.2) | Wisconsin (pH 5.4) |
| O—(Diaminophosphinyl)-2-propanone Oxime | 84 | 53 |

What is claimed is:

1. A urease inhibiting composition comprising a carrier and a urease inhibiting effective amount of one or more compounds of the formula:

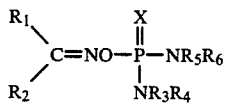

wherein:

X is oxygen or sulfur;

R₁ and R₂ are the same or different and are hydrogen, substituted or unsubstituted alkyl or aryl groups or R₁ and R₂ together may form a substituted or unsubstituted divalent aliphatic chain completing a cycloaliphatic group, which may optionally include one or more divalent heteroatoms of oxygen, sulfur or nitrogen wherein permissible substituents include one or more alkyl, aryl, halogen, trihalomethyl, nitro, cyano, alkanoyl, alkyl, carboxylate, arylcarboxylate, alkoxy, hydroxy, alkylmercapto, arylmercapto, mercapto, amino, alkylamino, dialkylamino, arylamino, diarylamino, diaminophosphinyl, N-diaminophosphinyl, O-diaminophosphinyl, S-diaminophosphinyl, carbamoyl and carbamoyldiaminophosphinyl; and R₃, R₄, R₅ and R₆ are the same or different and are hydrogen or alkyl having from about 1 to about 4 carbon atoms.

2. A composition according to claim 1 wherein said urease inhibiting amounts is at least about 0.00001 weight percent based on the total weight of the composition.

3. A composition according to claim 2 wherein said amount is from about 0.0001 to about 98 weight percent.

4. A composition according to claim 3 wherein said amount is from about 0.002 to about 50 weight percent.

5. A composition according to claim 4 wherein said amount is from about 0.01 to about 20 weight percent.

6. A composition according to claim 1 wherein X is oxygen.

7. A composition according to claim 1 wherein X is sulfur.

8. A composition according to claim 1 wherein R₃, R₄, R₅ and R₆ are hydrogen.

9. A composition according to claim 1 wherein R₁ and R₂ are the same or different and are hydrogen, or substituted or unsubstituted alkyl or aryl, or R₁ and R₂ together form a cycloaliphatic group.

10. A composition according to claim 9 wherein R₁ and R₂ together form a cycloaliphatic group.

11. A composition according to claim 9 wherein R₁ and R₂ are the same or different and are hydrogen, or unsubstituted aryl or alkyl.

12. A composition according to claim 11 wherein R₁ and R₂ are the same or different and are hydrogen, aryl or primary alkyl provided that at least one of R₁ and R₂ is a primary alkyl or hydrogen.

13. A composition according to claim 12 wherein R₁ is hydrogen and R₂ is alkyl or aryl.

14. A composition according to claim 13 wherein R₂ is phenyl or alkyl having from about 1 to about 8 carbon atoms.

15. A composition according to claim 14 wherein R₂ is primary alkyl having from 1 to about 8 carbon atoms.

16. A composition according to claim 12 wherein R₁ is alkyl and R₂ is alkyl or aryl.

17. A composition according to claim 16 wherein R₂ is alkyl.

18. A composition according to claim 17 wherein R₂ is aryl.

19. A composition according to claim 1 which comprises a urease inhibiting effective amount of O-(diaminophosphinyl)-2-propanone oxime.

20. A fertilizer composition which comprises urea and/or one or more urea precursor compounds capable of forming urea in situ when subjected to the use conditions of the composition, and a urease inhibiting effective amount of one or more compounds of the formula:

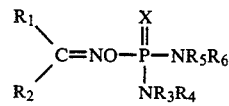

wherein:

X is oxygen or sulfur;

R₁ and R₂ are the same or different and are hydrogen, substituted or unsubstituted alkyl or aryl groups or R₁ and R₂ together may form a substituted or unsubstituted divalent aliphatic chain completing a cycloaliphatic group, which may optionally include one or more divalent heteroatoms of oxygen, sulfur or nitrogen wherein permissible substituents include one or more alkyl, aryl, halogen, trihalomethyl, nitro, cyano, alkanoyl, alkyl, carboxylate, arylcarboxylate, alkoxy, hydroxy, alkylmercapto, arylmercapto, mercapto, amino, alkylamino, dialkylamino, arylamino, diarylamino, diaminophosphinyl, N-diaminophosphinyl, O-diaminophosphinyl, S-diaminophosphinyl, carbamoyl and carbamoyldiaminophosphinyl; and R₃, R₄, R₅ and R₆ are the same or different and are hydrogen or alkyl having from about 1 to about 4 carbon atoms.

21. A composition according to claim 20 wherein X is oxygen.

22. A composition according to claim 20 wherein X is sulfur.

23. A composition according to claim 20 wherein R₃, R₄, R₅ and R₆ are hydrogen.

24. A composition according to claim 20 wherein R₁ and R₂ are the same or different and are hydrogen, or substituted or unsubstituted alkyl or aryl, or R₁ or R₂ together form a cycloaliphatic group.

25. A composition according to claim 24 wherein R₁ and R₂ are the same or different and are hydrogen, or unsubstituted aryl or alkyl.

26. A composition according to claim 25 wherein R₁ and R₂ are the same or different and are hydrogen, aryl or primary alkyl provided that at least one of R₁ and R₂ is primary alkyl or hydrogen.

27. A composition according to claim 26 wherein R₁ is hydrogen or alkyl and R₂ is alkyl or aryl.

28. A composition according to claim 27 wherein R₂ is phenyl or alkyl.

29. A composition according to claim 28 wherein R₂ is alkyl having from 1 to about 8 carbon atoms.

30. A composition according to claim 20 which comprises a urease inhibiting effective amount of O-(diaminophosphinyl)-2-propanone oxime.

31. A compound of the formula:

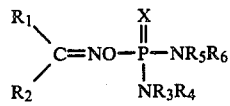

wherein:

X is oxygen or sulfur;

$R_1$ and $R_2$ are the same or different and are hydrogen, substituted or unsubstituted alkyl or aryl groups or $R_1$ and $R_2$ together may form a substituted or unsubstituted divalent aliphatic chain completing a cycloaliphatic group, which may optionally include one or more divalent heteroatoms of oxygen, sulfur or nitrogen wherein permissible substituents include one or more alkyl, aryl, halogen, trihalomethyl, nitro, cyano, alkanoyl, alkyl, carboxylate, arylcarboxylate, alkoxy, hydroxy, alkylmercapto, arylmercapto, mercapto, amino, alkylamino, dialkylamino, arylamino, diarylamino, diaminophosphinyl, N-diaminophosphinyl, O-diaminophosphinyl, S-diaminophosphinyl, carbamoyl and carbamoyldiaminophosphinyl; and $R_3$, $R_4$, $R_5$ and $R_6$ are the same or different and are hydrogen or alkyl having from about 1 to about 4 carbon atoms.

* * * * *